United States Patent [19]

Sakamoto et al.

[11] Patent Number: 4,528,410
[45] Date of Patent: Jul. 9, 1985

[54] PROCESS FOR PREPARATION OF ALCOHOLS BY HYDRATION OF OLEFINS

[75] Inventors: Teruhisa Sakamoto; Satoshi Ishida, both of Shinnanyo; Toshio Hironaka; Yukihiro Tsutsumi, both of Tokuyama, all of Japan

[73] Assignee: Toyo Soda Manufacturing Co., Ltd., Shinnanyo, Japan

[21] Appl. No.: 541,561

[22] Filed: Oct. 13, 1983

[30] Foreign Application Priority Data

Oct. 13, 1982 [JP] Japan .................................. 57-178298
Oct. 14, 1982 [JP] Japan .................................. 57-179101
Feb. 4, 1983 [JP] Japan .................................. 58-16236

[51] Int. Cl.$^3$ .............................................. C07C 29/04
[52] U.S. Cl. .................................................... 568/897
[58] Field of Search ........................................ 568/897

[56] References Cited

U.S. PATENT DOCUMENTS 4,214,107  7/1980  Chang et al. ...................... 568/897

Primary Examiner—J. E. Evans
Attorney, Agent, or Firm—Cushman, Darby & Cushman

[57] ABSTRACT

Olefins are hydrated to the corresponding alcohols in the presence of at least one crystalline alumino-silicate selected from offretite, ferrierite and erionite. The offretite, ferrierite and erionite are preferably characterized by X-ray diffraction patterns shown in Tables 1 and 7; Tables 2, 8 and 9; and Table 3, respectively. At least a part of the exchangeable cations in the offretite, ferrierite and erionite may be exchanged with at least one cation selected from a hydrogen ion, an alkaline earth metal ion and a rare earth metal ion. Furthermore, at least a part of the exchangeable cations in the erionite may be exchanged with an ammonium ion and/or an alkali metal ion.

18 Claims, No Drawings

PROCESS FOR PREPARATION OF ALCOHOLS BY HYDRATION OF OLEFINS

BACKGROUND OF THE INVENTION

1. Field of the Invention

This invention relates to a process for preparing an alcohol by hydrating an olefin in the presence of a catalyst. More particularly, it relates to a process for reacting an olefin with water to prepare a corresponding alcohol in the presence of a crystalline aluminosilicate, as a catalyst, which is selected from offretite, ferrierite and erionite.

2. Description of the Prior Art

A process for hydrating an olefin, especially a lower olefin such as ethylene, propylene or butene, to prepare a corresponding alcohol such as ethanol, propanol or butanol, is industrially important. Various processes are known for this hydration reaction, but a process using a mineral acid such as sulfuric acid or phosphoric acid is industrially adopted.

A vapor phase process using a phosphoric acid supported on a silica gel is industrially adopted for preparing ethanol by the hydration of ethylene. In this process, however, phosphoric acid supported on the silica gel is eluted whereby the activity is degraded. Accordingly, it is necessary to perpetually add phosphoric acid. Therefore, problems arise in connection with the treatment of the discharged waste liquid and the corrosion of the material of equipment. Furthermore, a large quantity of energy is necessary for recovery of unreacted ethylene or separation and purification of the produced ethanol because the conversion of ethylene is low.

A liquid phase process using sulfuric acid is widely adopted on the hydration of propylene or butenes, industrially. However, in this process, a large quantity of energy is necessary for hydrolysis of a sulfuric acid ester once formed and concentration and regeneration of the diluted aqueous sulfuric acid solution and equipment is violently corroded by the acid at high temperatures.

From equilibrium considerations, it is preferred that the hydration of olefins be carried out at a low temperature under a high pressure, and ordinarily, these reaction conditions provide high conversions of olefins to alcohols. However, it is necessary to obtain an industrially satisfactory rate of reaction, and practically, severe conditions of high temperatures and high pressures are adopted for obtaining such a high rate of reaction. For these reasons, it is eagerly desired to develop a highly active solid acid catalyst for the hydration of olefins, which is capable of reducing the consumption of energy and not causing corrosion of equipment or other trouble.

Attempts have heretofore been made to use solid catalysts for the hydration of olefins. For example, there have been proposed processes using complex oxides composed of silica, alumina, zirconia, titanium oxide, molybdenum oxide and tungsten oxide, metal phosphates such as aluminum phosphate and zirconium phosphate, and crystalline aluminosilicates called "zeolites" such as mordenite and Y type zeolite. However, these catalysts possess a low activity and the activity is gradually degraded when the reaction is carried out at a high temperature.

As the process using as a catalyst a crystalline aluminosilicate, which is relevant to the process of the present invention, there can be mentioned a process using a ZSM-5 type zeolite, which is disclosed in Japanese Unexamined Patent Publication No. 57-70,828.

A zeolite has a peculiar fine pore structure based on its characteristic crystal structure, and since it has a strong solid acidity, it is expected that it will probably be used as a catalyst. We examined various zeolites in connection with their activities for hydration of olefins, and it was confirmed that when zeolites heretofore proposed are used as the catalyst, the activity is not satisfactorily high, large quantities of by-products such as olefin oligomers, aldehydes and ketones are ordinarily formed, the selectivity to the intended alcohol is low and the activity is reduced by coking in many cases.

SUMMARY OF THE INVENTION

It is the primary object of the present invention to provide a crystalline aluminosilicate catalyst advantageously used for hydration of olefins to the corresponding alcohols, which has a very high activity for the hydration reaction of olefins and exhibits a stable catalytic performance with a high selectivity without reduction of the activity due to coking.

Other objects and advantages of the present invention will be apparent from the following description.

In accordance with the present invention, there is provided a process for the preparation of alcohols by catalytically hydrating olefins wherein at least one crystalline aluminosilicate is selected from the group consisting of offretite, ferrierite and erionite is used as a catalyst.

DESCRIPTION OF THE PREFERRED EMBODIMENTS

Offretite catalyst

Offretite is a crystalline aluminosilicate ordinarily having a silica/alumina molar ratio of from 5 to 10, containing sodium and potassium ions as alkali metal cations and having a chemical composition represented by the following formula:

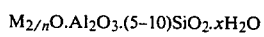

$$M_{2/n}O \cdot Al_2O_3 \cdot (5-10)SiO_2 \cdot xH_2O$$

wherein M stands for a cation having a valency of n, the coefficient of $M_{2/n}$ is a variable close to 1, and x is the number of at least 0, ordinarily from 0 to 10.

Crystallographically, offretite belongs to the hexagonal group, and it is known that offretite has lattice constants of a 13.3 Å and c=7.59 Å and a structure including chennels of 12-membered rings of oxygen atoms parallel to the axis c and channels of 8-membered rings of oxygen atoms parallel to the axis a. Characteristic crystal structure and X-ray diffraction pattern of offretite are shown in Journal of Catalysis, volume 20, pages 88–96 (1971).

Offretite is naturally present, but ordinarily, it can be synthesized by using a tetramethylammonium ion (TMA) under hydrothermal conditions. The process for synthesizing offretite by using TMA is disclosed, for example, in U.S. Pat. No. 3,578,398. The crystal structure of zeolite is generally determined according to the X-ray diffractometry, and one zeolite is distinguished from other zeolites by the X-ray diffraction pattern. In the above U.S. patent, the characteristic powder X-ray diffraction pattern of offretite is disclosed, which is as shown in Table 1 given hereinafter. Namely, offretite is characterized in that very strong X-ray diffraction peaks appear at $2\theta=7.7°$ and 23.7°, strong peaks appear at $2\theta = 13.4°, 20.5°, 24.9°$ and $31.4°$, and moderate peaks appear at $2\theta = 11.8°, 14.1°, 15.4°, 19.4°, 26.9°, 28.3°$ and $30.5°$. Incidentally, $2\theta$ means the diffraction angle obtained when the powder X-ray diffractometry is carried out by using a CuK$\alpha$ doublet, and the value of the lattice spacing d is calculated from the diffraction angle.

TABLE 1

Powder X-Ray Diffraction Pattern of Offretite

| Diffraction Angle $2\theta$ (°) | Lattice Spacing d (Å) | Relative Diffraction Intensity I/Io |
|---|---|---|
| 7.7 | 11.45 | 100 |
| 11.75 | 7.54 | 16.5 |
| 13.4 | 6.63 | 55.2 |
| 14.06 | 6.30 | 9.9 |
| 15.43 | 5.74 | 15.0 |
| 19.42 | 4.57 | 26.5 |
| 20.47 | 4.34 | 43.3 |
| 23.7 | 3.76 | 89.2 |
| 24.85 | 3.59 | 43.0 |
| 26.9 | 3.31 | 18.6 |
| 28.3 | 3.15 | 17.4 |
| 30.5 | 2.93 | 9.5 |
| 31.35 | 2.85 | 79.7 |
| 33.32 | 2.68 | 19.1 |
| 35.90 | 2.51 | 13.8 |

The process for the synthesis of offretite to be used in the present invention is not particularly critical. As an example of the process for the synthesis of offretite, the process disclosed in the above U.S. patent will now be described.

Colloidal silica or sodium silicate is used as a silica source, sodium aluminate is used as an alumina source, sodium hydroxide is used as a sodium source, potassium hydroxide is used as a potassium source, and tetramethylammonium chloride or tetramethylammonium hydroxide is used as a tetramethylammonium cation. Aqueous solutions of these starting materials are mixed together so that the following oxide molar ratios are attained:

$R_2O/(R_2O + Na_2O + K_2O) = 0.01 - 0.50$, $(R_2O + Na_2O + K_2O)/SiO_2 = 0.2 - 0.80$, $SiO_2/Al_2O_3 = 10-50$, and $H_2O/(R_2O + Na_2O + K_2O) = 25-45$ wherein R stands for tetramethyl ammonium cation. The formed aqueous gel is heated at a temperature of about 100° C. for about 20 hours to about 10 days, whereby offretite is synthesized.

In the as-synthesized zeolite, tetramethylammonium cations are contained as cations with potassium and sodium. Accordingly, when the as-synthesized zeolite is calcined in air at a temperature of about 500° to about 600° C., a part of the ion-exchangeable cations can be converted to hydrogen ions.

The ion-exchangeable cations of the offretite to be used as the catalyst in the process of the present invention are usually ion-exchanged with hydrogen ions. As the ion exchange process, there may be adopted the above-mentioned and other known ion-exchange processes. For example, ion exchange is effected in an aqueous solution by using an ammonium salt such as ammonium chloride or ammonium sulfate and calcination is then carried out. The degree of the ion exchange is such that at least about 30%, preferably at least about 70%, of the ion-exchangeable cations are converted to hydrogen ions. If necessary, the ion-exchangeable cations of the offretite may be ion-exchanged with alkali metal ions other than sodium and potassium, with alkaline earth metal ions such as calcium and magnesium, or with rare earth element ions such as lanthanum and cerium. Furthermore, chromium, manganese, iron, copper, zinc, phosphorus, molybdenum, tungsten, tin, antimony, bismuth or other element may be included into the offretite by the ion-exchange, impregnation or the like.

Ferrierite catalyst

Ferrierite is a crystalline aluminosilicate having a chemical composition generally represented by the following formula:

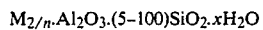

$M_{2/n} \cdot Al_2O_3 \cdot (5-100)SiO_2 \cdot xH_2O$ wherein M stands for a cation having a valency of n, the coefficient of $M_{2/n}$ is the variable close to 1, and x is number of at least 0, ordinarily from 0 to 10.

The crystal structure of ferrierite is disclosed, for example, in Journal of Catalysis, volume 35, pages 256 to 272 (1974). Namely, ferrierite is a zeolite having channels composed of 10-membered rings of oxygen atoms, and the effective pore size is about 5 Å. Generally, the crystal structure of a zeolite is determined by the X-ray diffractometry and one zeolite is distinguished from other zeolites by the X-ray diffraction pattern. As a typical instance of the X-ray diffraction of ferrierite, the powder X-ray diffraction pattern of ferrierite disclosed in the above reference is shown in Table 2.

TABLE 2

Powder X-ray Diffraction Pattern of Ferrierite

| Lattice Spacing d (Å) | Relative Intensity I/Io | Plane Index hkl |
|---|---|---|
| 9.41 | 100 | 200 |
| 7.00 | 24 | 020 |
| 6.56 | 24 | 011 |
| 5.72 | 12 | 310 |
| 5.61 | 12 | 220 |
| 3.97 | 45 | 031 |
| 3.92 | 37 | 420 |
| 3.83 | 27 | 411 |
| 3.75 | 40 | 330 |
| 3.65 | 34 | 510 |
| 3.52 | 65 | 040 |
| 3.47 | 58 | 202 |
| 3.30 | 15 | 240 |
| 3.15 | 28 | 312 |
| 3.04 | 20 | 431 |
| 2.94 | 10 | 530 |
| 2.88 | 10 | 620 |
| 2.56 | 3 | 350 |

The process for the synthesis of ferrierite is disclosed in Japanese Unexamined Patent Publications No. 50-127,898 and No. 55-85,415 in addition to the above reference. Ferrierite to be used in the present invention can be prepared according to any of the known processes. As an example, the process disclosed in Japanese Unexamined Patent Publication No. 50-127,898 will now be described.

Aqueous solutions of an alkali metal hydroxide or alkaline earth metal hydroxide, alumina or an alkali metal aluminate, a colloidal silica sol or alkali metal silicate and N-methylpyridinium hydroxide are mixed together so that the following oxide molar ratios are attained:

$SiO_2/Al_2O_3 = 5-160$, $(M_{2/n}O + R_2O)/SiO_2 = 0.07-1.8$, $(M_{2/n}O + R_2)/R_2O = 0.5-20$, and $H_2O/(M_{2/n}O + R_2O) = 50-170$ wherein M stands for an alkali metal or alkaline earth metal having a valency of n and R stands for N-methylpyridinium cation.

The formed aqueous gel was heated at about 140° to about 160° C. for several days, whereby ferrierite is synthesized.

In the process of the present invention, ferrierite is ordinarily used after conversion to a hydrogen type. For this purpose, known ion exchange processes are adopted. For example, ion exchange is effected in an aqueous solution by using an ammonium salt such as ammonium chloride or ammonium sulfate and calcination is then carried out, or conversion of the cations to hydrogen ions can be performed by a treatment in an aqueous solution by using hydrochloric acid. The degree of the ion exchange is such that at least about 30%, preferably at least about 70%, of the ion-exchangeable cations are converted to hydrogen ions. If necessary, the ion-exchangeable cations of the ferrierite may be ion-exchanged with alkali metal ions, alkaline earth metal ions such as calcium and magnesium, or rare earth element ions such as lanthanum and cerium. Furthermore, chromium, manganese, iron, copper, zinc, phosphorus, molybdenum, tungsten, tin, antimony, bismuth or other element may be included into the offretite by the ion-exchange, impregnation or the like.

Erionite catalyst

The crystal structure of erionite is ordinarily determined by the X-ray diffractometry. The powder X-ray diffraction pattern of erionite is shown in Table 3.

TABLE 3

| Powder X-Ray Diffraction Pattern of Erionite | | |
|---|---|---|
| Diffraction Angle $2\theta$ (°) ±0.2° | Lattice Spacing d (Å) ±0.2 Å | Relative Intensity |
| 7.7 | 11.5 | Very Strong |
| 9.6 | 9.2 | Weak or Medium |
| 11.7 | 7.6 | " |
| 13.4 | 6.6 | Strong |
| 14.0 | 6.3 | Weak or Medium |
| 15.5 | 5.7 | " |
| 16.5 | 5.4 | " |
| 17.8 | 5.0 | Weak |
| 19.4 | 4.6 | Weak or Medium |
| 20.5 | 4.3 | Strong |
| 21.4 | 4.2 | Weak or Medium |
| 23.4 | 3.8 | Strong |
| 23.7 | 3.7 | Strong or Very Strong |
| 24.8 | 3.6 | Medium or strong |
| 26.1 | 3.4 | Weak |
| 27.0 | 3.3 | Medium |
| 28.2 | 3.2 | " |
| 28.7 | 3.1 | Weak |
| 30.5 | 2.9 | Weak or Medium |
| 31.4 | 2.8 | Strong |
| 31.8 | 2.8 | Weak or Medium |
| 33.5 | 2.7 | " |

TABLE 3-continued

| Powder X-Ray Diffraction Pattern of Erionite | | |
|---|---|---|
| Diffraction Angle $2\theta$ (°) ±0.2° | Lattice Spacing d (Å) ±0.2 Å | Relative Intensity |
| 36.0 | 2.5 | " |
| 36.2 | 2.5 | " |
| 38.2 | 2.4 | Weak |
| 39.4 | 2.3 | " |

As a zeolite having an X-ray diffraction pattern similar to that of erionite, there can be mentioned offretite. Erionite is distinguished from offretite by the presence of X-ray diffraction peaks in the vicinity of diffraction angles $2\theta = 9.6°$, 16.5°, 21.4° and 28.7°, as determined by using a Cu-Kα ray, which correspond to erionite plane indexes of 101, 201, 211 and 311, respectively, called "l odd lines".

The crystal structure of erionite is disclosed, for example, in Journal of Catalysis, volume 20, pages 88 to 96 (1971). The crystal structure of erionite belongs to the hexagonal group. The lattice constants are a = 13.3 Å and c = 15.2 Å and erionite has channels of 8-membered rings of oxygen atoms parallel to the axis a.

Erionite is a crystalline aluminosilicate in which the silica/alumina molar ratio is ordinarily in the range of from about 5 to about 10 and sodium ions and potassium ions are contained as alkali metal cations. Erionite is naturally present, but it may be synthesized by a hydrothermal reaction ordinarily using an organic mineralizer such as a benzyltrimethylammonium cation. For example, Japanese Examined Patent Publication No. 50-23,400 discloses a process for synthesizing erionite by using a benzyltrimethylammonium cation. Furthermore, erionite can be synthesized according to a process not using an organic mineralizer. For example, this process is disclosed in Japanese Examined Patent Publication No. 44-30,613.

The above-mentioned patent publications and Japanese Unexamined Patent Publication No. 53-58,499 disclose specific powder X-ray diffraction patterns of erionite characterized by the X-ray diffraction pattern shown in Table 3. These specific powder X-ray diffraction patterns are shown in Tables 4 through 6.

TABLE 4

| Powder X-Ray Diffraction Pattern of Erionite (shown in Japanese Examined Patent Publication No. 44-30,613) | | | |
|---|---|---|---|
| Lattice Spacing d (Å) | Plane Index hkl | Relative Intensity of Natural Erionite I/Io | Relative Intensity of Synthetic Erionite I/Io |
| 11.46 | 100 | 100 | 100 |
| 9.14 | 101 | 8.5 | — |
| 7.55 | 002 | 7.8 | 4.0 |
| 6.61 | 110 | 40.6 | 41.4 |
| 6.30 | 102 | 4.9 | 2.8 |
| 5.72 | 200 | 5.3 | 3.3 |
| 5.35 | 201 | 6.9 | — |
| 4.61 | 103 | 4.1 | — |
| 4.56 | 202 | 5.8 | 3.9 |
| 4.33 | 210 | 24.8 | 30.6 |
| 4.16 | 211 | 10.9 | 4.5 |
| 3.81 | 300 | 14.2 | 12.1 |
| 3.75 | 212 | 40.4 | 36.0 |
| 3.58 | 104 | 21.3 | 14.9 |
| 3.40 | 302 | 0.7 | 0.7 |
| 3.30 | 220 | 16.6 | 10.6 |
| 3.28 | 213 | 6.2 | 1.3 |
| 3.17 | 310 | 6.6 | 5.1 |
| 3.15 | 204 | 12.6 | 11.5 |
| 3.10 | 311 | 3.3 | — |
| 2.92 | 312 | 6.5 | 4.4 |

TABLE 4-continued

Powder X-Ray Diffraction Pattern of Erionite (shown in Japanese Examined Patent Publication No. 44-30,613)

| Lattice Spacing d (Å) | Plane Index hkl | Relative Intensity of Natural Erionite I/Io | Relative Intensity of Synthetic Erionite I/Io |
|---|---|---|---|
| 2.86 | 400 | 26.8 | 29.6 |
| 2.84 | 214 | 21.0 | 25.2 |
| 2.81 | 401 | 21.8 | 5.7 |
| 2.67 | 402 | 7.3 | 6.9 |
| 2.51 | 006 | 1.3 | — |
| 2.50 | 410 | 5.6 | 5.6 |
| 2.48 | 322 | 8.8 | 10.4 |

TABLE 5

Powder X-Ray Diffraction Pattern of Synthetic Erionite (shown in Japanese Examine Patent Publication No. 50-23,400)

| Diffraction Angle 2θ | Lattice Spacing d (Å) | Relative Intensity I/Io |
|---|---|---|
| 7.70 | 11.5 | 100 |
| 9.6 | 9.2 | 19 |
| 11.65 | 7.60 | 19 |
| 13.4 | 6.59 | 52 |
| 14.0 | 6.32 | 16 |
| 15.45 | 5.73 | 27 |
| 16.55 | 5.34 | 22 |
| 17.6 | 5.03 | 1 |
| 17.9 | 4.94 | 1 |
| 19.45 | 4.57 | 25 |
| 20.55 | 4.32 | 74 |
| 21.4 | 4.15 | 34 |
| 23.4 | 3.81 | 62 |
| 23.7 | 3.75 | 75 |
| 24.75 | 3.59 | 54 |
| 26.2 | 3.40 | 6 |
| 27.05 | 3.30 | 31 |
| 28.3 | 3.16 | 34 |
| 28.7 | 3.10 | 4 |
| 30.6 | 2.91 | 13 |
| 31.4 | 2.83 | 74 |
| 31.9 | 2.80 | 26 |
| 33.55 | 2.665 | 17 |
| 36.1 | 2.48 | 21 |
| 36.35 | 2.475 | 3 |
| 38.15 | 2.36 | 3 |
| 39.5 | 2.28 | 4 |

TABLE 6

Powder X-Ray Diffraction Pattern of Erionite (shown in Japanese Unexamined Patent Publication No. 53-58,499)

| Diffraction Angle 2θ (°) | Lattice Spacing d (Å) | Erionite Relative Intensity I/Io | Erionite Plane Index hkl | Offretite Relative Intensity I/Io | Offretite Plane Index hkl |
|---|---|---|---|---|---|
| 7.72 | 11.5 | 83 | 100 | 99 | 100 |
| 9.69 | 9.2 | 38 | 101 | — | |
| 11.73 | 7.6 | 25 | 002 | 39 | 001 |
| 13.41 | 6.6 | 69 | 110 | 67 | 110 |
| 14.02 | 6.3 | 19 | 102 | 31 | 101 |
| 15.49 | 5.7 | 22 | 200 | 30 | 200 |
| 16.57 | 5.4 | 21 | 201 | — | |
| 17.79 | 5.0 | 12 | | 10 | |
| 19.46 | 4.6 | 29 | 202 | 42 | 201 |
| 20.54 | 4.3 | 60 | 210 | 69 | 210 |
| 21.37 | 4.2 | 34 | 211 | — | |
| 23.35 | 3.81 | 48 | 300 | 46 | 300 |
| 23.75 | 3.74 | 64 | 212 | 83 | 211 |
| 24.36 | 3.65 | 20 | | — | |
| 24.87 | 3.58 | 47 | 104 | 62 | 102 |
| 26.24 | 3.39 | 9 | 302 | 5 | 301 |
| 26.99 | 3.30 | 32 | 220 | 36 | 220 |
| 27.26 | 3.27 | 25 | 213 | 18 | |
| 28.15 | 3.17 | 18 | 310 | 18 | 310 |
| 28.36 | 3.14 | 34 | 204 | 47 | 202 |
| 28.79 | 3.10 | 10 | 311 | — | |
| 30.54 | 2.92 | 17 | 312 | 11 | 311 |
| 31.26 | 2.86 | 41 | 400 | 44 | 400 |
| 31.54 | 2.83 | 61 | 214 | 73 | 212 |
| 31.92 | 2.80 | 39 | 401 | — | 401 |
| 33.54 | 2.67 | 28 | 402 | 23 | |
| 34.71 | 2.58 | 15 | | — | |
| 35.80 | 2.51 | 18 | 006 | | |
| 35.98 | 2.49 | 30 | 410 | 8 | 410 |
| 36.22 | 2.48 | 24 | 322 | 25 | 411 |

Erionite is clearly distinguished from offretite by the adsorption properties as well as the X-ray diffraction pattern.

Since erionite has a channel structure based on 8-membered rings of oxygen atoms while offretite has a channel structure based on 12-membered rings of oxygen atoms, erionite is characterized in that the adsorption capacity of cyclohexane having a large molecule diameter is smaller than the adsorption capacity of n-hexane.

From the viewpoint of the catalyst performance, such as the activity, selectivity and life, it is preferred that erionite zeolite having a high purity and a high crystallinity be used in the process of the present invention. If the easy availability is taken into consideration in addition to the above properties, synthetic erionite is especially preferred. The process for the synthesis of the erionite type zeolite is not particularly critical, but from the economical viewpoint, a process not using an organic mineralizer is preferred.

The ion-exchangeable cations of the erionite to be used as the catalyst in the process of the present invention are ion-exchanged with hydrogen ions. As the ion exchange process, there may be adopted known ion-exchange process. For example, ion exchange is effected in an aqueous solution by using an ammonium salt such as ammonium chloride, ammonium sulfate or ammonium nitrate and calcination is then carried out. The degree of the ion exchange is such that at least about 30%, preferably at least about 70%, of the ion-exchangeable cations are converted to hydrogen ions. If necessary, the ion-exchangeable cations of the erionite may be ion-exchanged with alkali metal ions other than sodium and potassium, with alkaline earth metal ions such as calcium and magneisum, or with rare earth element ions such as lanthanum and cerium. Furthermore, chromium, manganese, iron, copper, zinc, phosphorus, molybdenum, tungsten, tin, antimony, bismuth or other element may be included into the erionite by the ion-exchange, impregnation or the like.

Preparation of Catalyst

The shape of the catalyst is not particularly critical. For example, the catalyst may be used in the form of a powder, a granule, a sphere or a pellet. The catalyst may be molded by spray-dry granulation, extrusion molding or compression molding. If necessary, silica, alumina, silica-alumina, clay, activated clay, titanium oxide or zirconia may be added to improve the mechanical strength of the molded catalyst. The catalyst is ordinarily calcined in air at a temperature of about 300° to about 600° C.

Hydration of Olefins

Hydration of an olefin can be carried out in either the vapor phase or the liquid phase, and a known reaction method such as a fixed bed method, a fluidized bed method or suspended bed method may be adopted. Various olefins can be used as the starting olefin, but ordinarily, olefins having 2 to 8 carbon atoms are preferred and lower olefins having 2 to 4 carbon atoms, such as ethylene, propylene and butene, are especially preferred. The hydration reaction of an olefin is an equilibrium reaction to the reverse reaction, that is, the dehydration reaction of an alcohol, and a low temperature and a high pressure are ordinarily advantageous for the formation of an alcohol. However, preferred conditions greatly differ according to the particular starting olefin. From the viewpoint of the rate of reaction, a higher temperature is preferred. Accordingly, it is difficult to simply define the reaction conditions. However, a reaction temperature of about 50° to about 350° C. is ordinarily preferred and a reaction temperature of about 100° to about 300° C. is especially preferred. The reaction pressure is not particularly critical but a higher pressure is preferred from the viewpoint of the reaction equilibrium. From the industrial viewpoint, it is preferred that the reaction pressure be 1 to 300 atmospheres, especially 1 to 250 atmospheres. Also the molar ratio of water to the starting olefin is an important factor having significant influences on the reaction as well as the reaction temperature and pressure. From the viewpoint of the reaction equilibrium, a higher molar ratio of water to the starting olefin is advantageous and a high conversion of the olefin is obtained when this molar ratio is high. However, if the molar ratio of water to the olefin is too high, the concentration of the alcohol in the obtained reaction liquid is reduced and a large quantity of energy is necessary for separation and purification of the alcohol from the reaction liquid. On the other hand, if the molar ratio of water to the olefin is reduced, an aqueous solution having a high alcohol concentration can be obtained, but the conversion of the olefin is reduced and a side reaction such as polymerization is advanced. Accordingly, it is preferred that the molar ratio of water to the olefin be about 0.2 to about 100, especially 0.3 to 50. If the reaction is catalytically carried out in the vapor phase, mainly from the economical viewpoint, it is preferred that the molar ratio of water to the olefin be about 0.2 to about 30, especially 0.3 to 20.

A saturated hydrocarbon such as methane, ethane, propane or butane, an ether such as diethyl ether, a ketone such as acetone, an inert gas such as nitrogen or carbon dioxide, or hydrogen or other gas may be contained in the starting olefin. The contact time is varied depending upon the reaction method and reaction conditions. In case of the fixed bed method, the liquid hourly space velocity (LHSV) value of the starting olefin and water is preferably about 0.1 to about 20 hr$^{-1}$ and especially preferably about 0.5 to about 10 hr$^{-1}$. The alcohol produced by the reaction can be separated from the aqueous solution and purified according to customary procedures. The unreacted starting olefin can be recovered and recycled for reuse.

One of the characteristic features attained by using offretite, ferrierite and/or erionite as the catalyst in the process of the present invention is that the activity for the hydration reaction of olefins is higher than those of conventional catalysts such as mordenite, Y type zeolite and ZSM-5 type zeolite and the reactivity for polymerization or cracking is very low. Namely, the defects of the conventional catalysts such as reduction of the activity by coking or the like and loss of the starting olefin by polymerization or the like can be eliminated. Furthermore, it is possible to hydrate an olefin, which is readily polymerized, at a small molar ratio of water to the olefin, and the consumption of energy is reduced for the above-mentioned reason.

It has not clearly been elucidated what of such factors as the channel structure, the acidic property and other physical properties of the catalyst will produce the above-mentioned differences of the activity, but according to the process of the present invention, olefins can be converted to corresponding alcohols at a low temperature under mild conditions. Furthermore, according to the process of the present invention, olefins can be converted to corresponding alcohols at a high conversion and a high selectivity.

The present invention will now be described in detail with reference to the following examples that by no means limit the scope of the invention.

EXAMPLE 1

Offretite was synthesized according to the process disclosed in U.S. Pat. No. 3,578,398. More specifically, 2,235 g of colloidal silica (containing 30% by weight of SiO$_2$) was added to an aqueous solution comprising 105 g of sodium aluminate, 287 g of sodium hydroxide, 139 g of potassium hydroxide and 1,521 g of water. 216 g of an aqueous solution containing 50% by weight of tetramethyl ammonium chloride was further added to the solution to form a reaction mixture having a composition represented by the following formula:

$$1.54(TMA)_2O.6.60Na_2O.1.95K_2O.Al_2O_3.17.4SiO_2.284H_2O.$$

This composition corresponds to the following molar ratios:

$$R_2O/(R_2O+Na_2O+K_2O)=0.15,$$

$$(R_2O+Na_2O+K_2O)/SiO_2=0.58,$$

$$SiO_2/Al_2O_3=17.4,$$

and $$H_2O/(R_2O+Na_2O+K_2O)=28.2.$$

wherein R stands for tetramethylammonium cation. This reaction mixture was heated at 100° C. for 6 days to effect crystallization. The reaction mixture was cooled to room temperature, and the obtained solid crystal was recovered by filtration, washed and then dried. From the results of the powder X-ray diffractometry using a CuKα doublet, it was confirmed that the X-ray diffraction pattern was the same as that shown in Table 1. From the results of the elementary analysis, it was confirmed that the product had the following composition:

$$0.23(TMA)_2O.0.32Na_2O.0.45K_2O.Al_2O_3.6.7SiO_2.4.2H_2O.$$

The crystal was calcined at 540° C. in air for 3 hours and the ion exchange was carried out in an aqueous 2N ammonium chloride solution at 90° C. for 5 hours.

Then, the crystal was washed with water, dried and calcined again in air at 540° C. for 3 hours. From the results of the elementary analysis, the crystal was found to have the following composition:

0.006Na$_2$O.0.23K$_2$O.Al$_2$O$_3$.6.7SiO$_2$.4.6H$_2$O.

From the results of the powder X-ray diffractometry, it was found that the X-ray diffraction pattern was not changed by the ion exchange.

Hydration of ethylene was carried out by using the so-obtained crystalline powder as the catalyst. More specifically, an autoclave having a capacity of 200 ml was charged with 90 g (5.0 moles) of water, 2 g of the above catalyst and 8.2 g (0.293 mole) of ethylene, and then the mixture was heated at 250° C. with stirring for 2 hours to effect reaction. The pressure was about 120 kg/cm$^2$.

After completion of the reaction, the reaction mixture was cooled to room temperature and then the catalyst was separated by filtration. The reaction liquid was analyzed by gas chromatography. It was found that 1.82 g (0.0396 mole) of ethanol was produced. The conversion of ethylene to ethanol was 13.5%. Minute amounts of acetaldehyde and acetone were produced in addition to ethanol but production of other products was not observed. The selectivity based on ethylene was 97.0% to ethanol, 2.3% to acetaldehyde and 0.7% to acetone.

EXAMPLE 2

Hydration of propylene was carried out by using the same catalyst as used in Example 1. More specifically, an autoclave having a capacity of 200 ml was charged with 2 g of the catalyst, 90 g (5.0 moles) of water and 9.5 g (0.226 mole) of propylene, and then the mixture was heated at 180° C. with stirring for 2 hours to effect reaction. The pressure was about 70 kg/cm$^2$.

After completion of the reaction, the reaction mixture was cooled to room temperature, and then the catalyst was separated by filtration. The reaction liquid was analyzed by gas chromatography. It was confirmed that 1.45 g (0.0242 mole) of isopropanol was produced. The conversion of propylene to isopropanol was 10.7%. A minute amount of acetone was produced in addition to isopropanol. The selectivity to isopropanol was 98.7%.

EXAMPLE 3

To an aqueous solution comprising 32 g of sodium aluminate, 72 g of sodium hydroxide, 28 g of potassium hydroxide and 520 g of water was added 180 g of an aqueous solution containing 10% by weight of tetramethylammonium chloride, 720 g of a silica sol (containing 30% by weight of SiO$_2$) was further added to the solution to form a reaction mixture having the following composition:

0.42(TMA)$_2$O.5.60Na$_2$O.1.28K$_2$O.Al$_2$O$_3$.18.4SiO$_2$.343H$_2$O.

The reaction mixture was charged in an autoclave having a capacity of 2 liters and heated at 170° C. with stirring for 4 hours to effect crystallization. The reaction mixture was cooled to room temperature, and the solid crystal was recovered by filtration, washed with water and then dried.

From the results of the powder X-ray diffractometry using a CuKα doublet, it was found that the crystal had an X-ray diffraction pattern shown in Table 7. From the results of the elementary analysis, it was found that the crystal had the following composition:

0.23(TMA)$_2$O.0.36Na$_2$O.0.41K$_2$O.Al$_2$O$_3$.7.25SiO$_2$.3.7H$_2$O.

TABLE 7

Results of Powder X-ray Diffractometry of Zeolite of Example 3

| Diffraction Angle 2θ (°), ±0.2° | Lattice spacing d (Å), ±0.1 Å | Relative Intensity I/Io | Plane Index hkl |
|---|---|---|---|
| 7.7 | 11.5 | 100 | 100 |
| 11.7 | 7.6 | 29 | 001 |
| 13.4 | 6.6 | 64 | 110 |
| 14.1 | 6.3 | 22 | 101 |
| 15.4 | 5.7 | 21 | 200 |
| 19.4 | 4.6 | 42 | 201 |
| 20.5 | 4.3 | 60 | 210 |
| 23.3 | 3.8 | 37 | 300 |
| 23.7 | 3.8 | 116 | 211 |
| 24.8 | 3.6 | 89 | 102 |
| 26.1 | 3.4 | 2 | 301 |
| 26.9 | 3.3 | 22 | 220 |
| 28.1 | 3.2 | 18 | 310 |
| 28.3 | 3.2 | 36 | 202 |
| 30.5 | 2.9 | 12 | 311 |
| 31.2 | 2.9 | 78 | 400 |
| 31.4 | 2.8 | 97 | 212 |
| 33.4 | 2.7 | 19 | 401 |
| 35.9 | 2.5 | 14 | 410 |
| 36.2 | 2.5 | 18 | 411 |

The crystal was calcined at 540° C. for 3 hours in air and then the ion change was carried out in an aqueous 2N ammonium chloride solution at 90° C. for 5 hours. The crystal was recovered by filtration, washed with water, dried and then calcined again in air at 540° C. for 3 hours. From the results of the elementary analysis, it was found that the crystal had the following composition:

0.02Na$_2$O.0.24K$_2$O.Al$_2$O$_3$.7.1SiO$_2$.3.4H$_2$O.

From the results of the powder X-ray diffractometry, it was found that the X-ray diffraction pattern as observed before the ion exchange treatment was the same as that observed after the ion exchange treatment.

The so-obtained zeolite crystal powder was mixed with 15% by weight of kieselguhr, and then the mixture was extrusion-molded to a cylinder-like granule having a diameter of 3 mm. The molded granules were calcined in air at 540° C. for 3 hours to obtain a catalyst.

Hydration of ethylene was carried out under pressure by using a fixed bed reaction apparatus. More specifically, using 20 ml of the catalyst packed in a reaction tube, reaction was carried out at a temperature of 250° C., a pressure of 70 kg/cm$^2$, a water/ethylene molar ratio of 0.6 and a liquid hourly space velocity of water and ethylene of 1.0 hr$^{-1}$. The reaction product was sampled at predetermined intervals to analyze it by gas chromatography. It was found that the conversion of ethylene to ethanol was 5.7%, and minute amounts of acetaldehyde and acetone were produced in addition to ethanol. The selectivity to ethanol was 97.5%.

EXAMPLE 4

Hydration of propylene was carried out by using the same catalyst as used in Example 3 in the same manner as described in Example 3. More specifically, using 20 ml of the catalyst packed in a reaction tube, reaction was carried out at a temperature of 180° C., a pressure of 20 kg/cm², a water/propylene molar ratio of 1 and a liquid hourly space velocity of water and propylene of 1.0 hr⁻¹. The conversion of propylene to isopropanol was 5.2%. A minute amount of acetone was produced in addition to isopropanol. The selectivity to isopropanol was 99.0%.

EXAMPLE 5

Hydration of isobutene was carried out by using the same catalyst as used in Example 3 in the same manner as described in Example 3. More specifically, a reaction tube was packed with 20 ml of the catalyst, and reaction was carried out at a temperature of 120° C., a pressure of 10 kg/cm², a water/isobutene molar ratio of 1 and a liquid hourly space velocity of water and isobutene of 1.0 hr⁻¹. It was found that the conversion of isobutene to tert-butanol was 4.6%. The selectivity to tert-butanol was 100%.

EXAMPLE 6

Hydration of butene-1 was carried out by using the same catalyst as used in Example 3 in the same manner as described in Example 3. More specifically, 20 ml of the catalyst was packed in a reaction tube and reaction was carried out at a temperature of 160° C., a pressure of 10 kg/cm², a water/butene-1 molar ratio of 1 and a liquid hourly space velocity of water and butene-1 of 1.0 hr⁻¹. The conversion of butene-1 to sec-butanol was 2.4%. The selectivity to sec-butanol was 99.2%.

EXAMPLE 7

Ferrierite was synthesized according to the process disclosed in Japanese Unexamined Patent Publication No. 50-127,898. More specifically, 68.8 g of N-methylpyridinium iodide, 22.5 g of sodium hydroxide and 5.1 g of sodium aluminate were dissolved in 720 g of water. Then, 242 g of silica sol (containing 30% by weight of $SiO^2$) was added to the solution to obtain a reaction mixture having the following molar ratios:

$SiO_2/Al_2O_3 = 38.8$, $(Na_2O + R_2O)/SiO_2 = 0.39$, $H_2O/(Na_2O + R_2O) = 106$, and $Na_2O/R_2O = 2.0$ wherein R stands for N-methylpyridinium cation.

The reaction mixture was charged in an autocalve having a capacity of 2 liters and then heated at 150° C. for 6 days to effect crystallization. Then, the reaction mixture was cooled to room temperature, and the formed solid crystal was recovered by filtration, washed and then dried. From the results of the powder X-ray diffractometry of the obtained zeolite by using a CuKα doublet, it was confirmed that the zeolite had an X-ray diffraction pattern shown in Table 8, which corresponds to the X-ray diffraction pattern of ferrierite. From the results of the elementary analysis, it was found that the zeolite had the following composition:

$0.27R_2O \cdot 0.73Na_2O \cdot Al_2O_3 \cdot 28.3SiO_2 \cdot 5.7H_2O$.

TABLE 8

Results of Powder X-Ray Diffractometry of Zeolite of Example 7

| Diffraction Angle 2θ (°) | Lattice Spacing d (Å) | Relative Intensity I/Io | Plane Index hkl |
|---|---|---|---|
| 9.40 | 9.40 | 100 | 200 |
| 12.50 | 7.07 | 22 | 020 |
| 12.80 | 6.91 | 24 | |
| 13.40 | 6.60 | 22 | 011 |
| 15.40 | 5.75 | 20 | 310 |
| 15.70 | 5.64 | 10 | 220 |
| 17.86 | 4.96 | 10 | |
| 22.30 | 3.98 | 68 | 031 |
| 22.56 | 3.94 | 50 | 420 |
| 23.20 | 3.83 | 32 | 411 |
| 23.68 | 3.75 | 52 | 330 |
| 23.90 | 3.72 | 10 | |
| 24.46 | 3.63 | 35 | 510 |
| 25.20 | 3.53 | 94 | 040 |
| 25.77 | 3.45 | 92 | 202 |
| 26.50 | 3.36 | 16 | |
| 26.96 | 3.30 | 20 | 240 |
| 28.58 | 3.12 | 24 | 312 |
| 29.42 | 3.03 | 18 | 431 |
| 30.38 | 2.94 | 10 | 530 |
| 30.96 | 2.88 | 8 | 620 |

The crystal was calcined in air at 540° C. for 3 hours and then subjected to the ion exchange in an aqueous 2N ammonium chloride solution at 90° C. for 5 hours. The crystal was washed with water, dried and calcined again at 540° C. for 3 hours. From the results of the elmentary analysis, it was found that the product had the following composition:

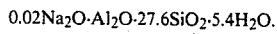

$0.02Na_2O \cdot Al_2O \cdot 27.6SiO_2 \cdot 5.4H_2O$.

From the results of the powder X-ray diffractometry, it was confirmed that the X-ray diffraction pattern as observed after the ion exchange treatment was the same as that as observed before the ion exchange treatment.

Hydration of ethylene was carried out by using the thus-obtained crystalline powder as the catalyst. More specifically, an autoclave having a capacity of 200 ml was charged with 72 g (4.0 moles) of water, 2 g of the above catalyst and 4.2 g (0.150 mole) of ethylene, and the mixture was heated at 250° C. with stirring for 2 hours to effect reaction. The pressure was about 70 kg/cm².

After completion of the reaction, the reaction mixture was cooled to room temperature and then the catalyst was separated by filtration, and the reaction liquid was analyzed by gas chromatography. It was found that 1.36 g (0.0296 mole) of ethanol was produced. The conversion of ethylene to ethanol was 19.7%. Minute amounts of acetaldehyde and acetone were produced in addition to ethanol but production of other products was not observed. The selectivity based on ethylene was 98.6% to ethanol, 1.2% to acetaldehyde and 0.2% to acetone.

EXAMPLE 8

Ferrierite having the following composition was synthesized in the same manner as described in Example 7:

$26R_2O \cdot 0.74Na_2O \cdot Al_2O_3 \cdot 17.3SiO_2 \cdot 5.0H_2O$ wherein R stands for N-methylpyridinium cation. The X-ray diffraction pattern of the ferrierite was the same as that shown in Table 2.

The ferrierite was calcined in air at 540° C. for 3 hours and then subjected to the ion exchange in an aqueous 1N hydrochloric acid solution at 90° C. for 5 hours. The crystal was washed with water, dried and calcined again at 500° C. in air for 3 hours. From the results of the elementary analysis, it was confirmed that the crystal had the following composition:

$0.003Na_2O \cdot Al_2O_3 \cdot 16.8SiO_2 \cdot 7.4H_2O.$

It was confirmed that the X-ray diffraction pattern as observed after the ion exchange treatment was the same as that as observed before the ion exchange treatment.

The thus-obtained crystal powder was mixed with alumina sol in an amount of 20% by weight as $Al_2O_3$, and then 5% by weight of graphie was further added. The mixture was molded to a tablet having a diameter of 5 mm and a height of 5 mm. The molded product was calcined in air at 540° C. for 3 hours to form a catalyst.

Hydration of ethylene was carried out under pressure by using a fixed bed reaction apparatus. More specifically, 20 ml of the catalyst was packed in a reaction tube and reaction was carried out at a temperature of 250° C., a pressure of 70 kg/cm$^2$, a water/ethylene molar ratio of 0.6 and a liquid hourly space velocity of water and etylene of 1.0 hr$^{-1}$. The reaction product was sampled at predetermined intervals and analyzed by gas chromatography. It was found that the conversion of ethylene to ethanol was 7.4%. The reaction was not particularly changed with time on stream. Minute amounts of acetaldehyde and acetone were produced in addition to ethanol, but other products were not produced. The selectivity to ethanol was 97.9%.

EXAMPLE 9

Hydration of propylene was carried out by using the same catalyst as used in Example 8 in the same manner as described in Example 8. More specifically, using 20 ml of the catalyst packed in a reaction tube, reaction was carried out at a temperature of 180° C., a pressure of 20 kg/cm$^2$, a water/propylene molar ratio of 1 and a liquid hourly space velocity of water and propylene of 1.0 hr$^{-1}$. The conversion of propylene to isopropanol was 6.7%. A minute amount of acetone was produced in addition to isopropanol. The selectivity to isopropanol was 99.6%.

EXAMPLE 10

Hydration of isobutene was carried out by using the same catalyst as used in Example 8 in the same manner as described in Example 8. More specifically, a reaction tube was packed with 20 ml of the catalyst, and reaction was carried out at a temperature of 120° C., a pressure of 10 kg/cm$^2$, a water/isobutene molar ratio of 1 and a liquid hourly space velocity of water and isobutene of 1.0 hr$^{-1}$. It was found that the conversion of isobutene to tert-butanol was 5.6%.

EXAMPLE 11

Ferrierite was synthesized according to the process disclosed in Japanese Unexamined Patent Publication No. 55-85,415. More specifically, piperidine was dissolved in an aqueous sodium silicate solution. An aqueous solution containing sulfuric acid and aluminum sulfate was added to the resulting solution to form a reaction mixture having the following composition:

$9Na_2O \cdot 18piperdine \cdot Al_2O_3 \cdot 47SiO_2 \cdot 5Na_2SO_4 \cdot 970 \cdot H_2O.$ The reaction mixture was heated at 150° C. for 5 days to effect crystallization. Then, the reaction mixture was cooled to room temperature and the formed solid crystal was recovered by filtration, washed and then dried. From the results of the powder X-ray diffractometry using a CuK$\alpha$ doublet, it was found that the obtained zeolite had an X-ray diffraction pattern shown in Table 9, which corresponds to the X-ray diffraction pattern of ferrierite. From the results of the elementary analysis, it was found that the product had the following composition:

$0.29R_2O \cdot 0.71Na_2O \cdot Al_2O_3 \cdot 24.7SiO_2 \cdot 4.0H_2O.$

TABLE 9
Results of Powder X-Ray Diffractometry of Zeolite of Example 11

| Diffraction Angle 2θ (°) | Lattice Spacing d (Å) | Relative Diffraction Intensity I/Io | Plane Index hkl |
|---|---|---|---|
| 9.38 | 9.42 | 100 | 200 |
| 12.48 | 7.08 | 13 | 020 |
| 12.72 | 6.95 | 14 | |
| 13.38 | 6.61 | 14 | 011 |
| 15.34 | 5.77 | 13 | 310 |
| 15.60 | 5.67 | 6 | 220 |
| 17.82 | 4.97 | 10 | |
| 22.28 | 3.99 | 56 | 031 |
| 22.57 | 3.93 | 30 | 420 |
| 23.06 | 3.85 | 20 | 411 |
| 23.50 | 3.78 | 31 | 330 |
| 23.78 | 3.74 | 7 | |
| 24.24 | 3.67 | 22 | 510 |
| 25.17 | 3.53 | 48 | 040 |
| 25.61 | 3.47 | 55 | 202 |
| 26.30 | 3.38 | 13 | |
| 26.90 | 3.31 | 16 | 240 |
| 27.70 | 3.22 | 5 | |
| 28.42 | 3.14 | 17 | 312 |
| 29.24 | 3.05 | 11 | 431 |
| 30.22 | 2.95 | 5 | 530 |
| 30.90 | 2.89 | 4 | 620 |

The crystal was calcined in air at 540° C. for 3 hours and then subjected to the ion exchange in an aqueous 1N hydrochloric acid solution at 90° C. for 5 hours. The crystal was recovered by filtration, washed with water, dried and then calcined in air at 540° C. for 3 hours. From the results of the elementary analysis, it was found that the crystal has the following composition:

$0.001Na_2O \cdot Al_2O_3 \cdot 25.3SiO_24.8H_2O.$

From the results of the power X-ray diffractometry, it was found that the X-ray diffraction pattern as observed after the ion exchange treatment was substantially the same as that as observed after the ion exchange treatment.

Hydration of ethylene was carried out by using the thus-obtained crystalline powder as the catalyst in the same manner as described in Example 7. More specifically, an autoclave having a capacity of 200 ml was charged with 90 g (5.0 moles) of water, 2 g of the above catalyst and 8.0 g (0.286 mole) of ethylene. The mixture was heated at 250° C. with stirring for 2 hours to effect reaction. The pressure was about 120 kg/cm$^2$.

After completion of the reaction, the reacion mixture was cooled to room temperature and then the catalyst was separated by filtration. The reaction liquid was analyzed by gas chromatography. It was found that 2.29 g (0.0498 mole) of ethanol was produced. The conversion of ethylene to ethanol was 17.4%. The selectivity based on ethylene to ethanol was 97.8%.

EXAMPLE 12

Hydration of propylene was carried out by using the same catalyst as used in Example 11 in the same manner as described in Example 11. More specifically, an autoclave having a capacity of 200 ml was charged with 2 g of the catalyst, 72 g (4.0 moles) of water and 13.6 g (0.324 mole) of propylene. The mixture was heated at 160° C. with stirring for 2 hours to effect reaction. The pressure was about 70 kg/cm$^2$.

When the liquid reaction mixture was analyzed by gas chromatography, it was found that 2.87 g (0.0478 mole) of isopropanol was produced. The conversion of propylene to isopropanol was 14.8%. A minute amount of acetone was produced in addition to isopropanol. The selectivity to isopropanol was 99.2%.

EXAMPLE 13

Hydratin of butene-1 was carried out by using the same catalyst as used in Example 11 in the same manner as described in Example 11. More specifically, an autoclave having a capacity of 200 ml was charged with 2 g of the catalyst, 72 g (4.0 moles) of wate and 18.5 g (0.330 mole) of butene-1. The mixture was heated at 160° C. with stirring for 2 hours to effect reaction. The pressure was about 60 kg/cm$^2$.

When the liquid reaction mixture was analyzed by gas chromatography, it was found that 1.80 g (0.0243 mole) of sec-butanol was produced. The conversion of butene-1 to sec-butanol was 6.5%.

COMPARISON EXAMPLE 1

ZSM-5 zeolite was prepared according to the process disclosed in U.S. Pat. No. 3,965,207. More specifically, a mixture comprising 55.0 g of silica gel, 26.4 g of sodium hydroxide and 110 g of water was heated at 80° C. to form a solution. To the solution were added 567 g of water, 6.1 g of aluminum sulfate, 16 g of sulfuric acid and 1.9 g of sodium chloride. Then 24 g of tetra-n-propylammonium was added, and the mixture was heated at 160° C. with stirring for 17 hours in an autoclave having a capacity of 2 liters to effect crystallization. The reaction mixture was cooled to room temperature, and the formed solid crystal was recovered by filtration, washed and then dried. From the results of the powder X-ray diffractometry, it was found that the X-ray diffraction pattern of the obtained zeolite was in agreement with that of ZSM-5. From the results of the elementary analysis, it was found that the zeolite had the following composition:

$$0.34R_2O \cdot 0.69Na_2O \cdot Al_2O \cdot 48.2SiO_2 \cdot 5.7H_2O$$

wherein R stands for tetra-n-propylammonium cation.

The obtained crystal was calcined in air at 540° C. for 3 hours and then subjected to the ion exchange in an aqueous 2N hydrochloric acid solution at 90° C. for 5 hours. The crystal was recovered by filtration, washed with water and calcined in air at 540° C. for 3 hours. From the results of the elementary analysis, it was found that the zeolite had the following composition:

$$0.001Na_2O \cdot Al_2O_3 \cdot 48.7SiO_2 \cdot 4.0H_2O.$$

Hydration of ethylene was carried out by using the so-obtained crystalline powder as the catalyst in the same manner as described in Example 7. More specifically, an autoclave having a capacity of 200 ml was charged with 72 g (4.0 moles) of water, 2 g of the above catalyst and 4.2 g (0.15 mole) of ethylene. The mixture was heated at 250° C. with stirring for 2 hours to effect reaction. The pressure was about 70 kg/cm$^2$.

After completion of the reaction, the reaction mixture was cooled to room temperature and then the catalyst was separated by filtration. The reaction liquid was analyzed by gas chromatography. It was found that 0.57 g (0.0124 mole) of ethanol was formed. The conversion of ethylene to ethanol was 8.3%. Minute amounts of acetaldehyde and acetone were produced in addition to ethanol. The selectivity based on ethylene was 94.7% to ethanol, 4.1% to acetaldehyde and 1.2% to acetone.

COMPARISON EXAMPLE 2

The ZSM-5 zeolite crystal powder obtained in Comparison Example 1 was mixed with alumina sol in an amount of 20% by weight as Al$_2$O$_3$ as in Example 8, and 5% by weight of graphite was further added. The mixture was molded to a tablet having a diameter of 5 mm and a height of 5 mm. The molded product was calcined in air at 540° C. for 3 hours to obtain a catalyst.

Hydration of ethylene was carried out in the same manner as described in Example 8. More specifically, using 20 ml of the catalyst packed in a reaction tube, reaction was carried out at a temperature of 250° C., a pressure of 70 kg/cm$^2$, a water/ethylene molar ratio of 0.6 and a liquid hourly space velocity of water and propylene of 1.0 hr$^{-1}$. The conversion of ethylene to ethanol was 3.5%. Acetaldehyde, acetone and minute amounts of hydrocarbons were produced in addition to ethanol. The selectivity based on ethylene was 94.1% to ethanol, 3.8% to acetaldehyde, 1.7% to acetone and about 0.4% to hydrocarbons.

EXAMPLE 14

Erionite was synthesized according to a process disclosed in Japanese Examined Patent Publicaton No. 44-30,613. More specifically, 20.4 g of sodium hydroxide (having a purity of 98% by weight), 29.7 g of potassium hydroxide (having a purity of 85% by weight) and 140.0 g of sodium aluminate (comprising 21.82% by weight of Al$_2$O$_3$ and 18.77% by weight of Na$_2$O) were dissolved in 265.2 g of water. Then, 204.0 g of powdery silica gel (having a purity of 88.2% by weight) was added to the solution to form a reaction mixture having the following molar ratios:

SiO$_2$/Al$_2$O$_3$=10, (Na$_2$O+K$_2$O)/SiO$_2$=0.3,

K$_2$O/(K$_2$O+Na$_2$O)=0.25, and

H$_2$O/SiO$_2$=7.

This reaction mixture was charged in an autoclave having a capacity of 1 liter and heated at 150° C. for 24 hours to effect crystallization. Then, the reaction mixture was cooled to room temperature, and the formed solid crystal was recovered by filtration, washed and then dried. From the results of the X-ray diffractometry, it was found that the product had an X-ray diffraction pattern corresponding to that shown in Table 3. When the adsorption capacity of the product was measured, it was found that the n-hexane adsorption capacity was 7.1% by weight and the cyclohexane adsorption capacity was 0.6% by weight, as determined at 25° C. and 48 mmHg.

The crystal powder was subjected to the ion exchange an aqueous 2N ammonium nitrate solution at 90° C. for 5 hours. The crystal was washed with water, dried and calcined in air at 540° C. for 5 hours to convert the zeolite to a hydrogen type.

Hydration of ethylene was carried out by using the thus-obtained crystalline powder as the catalyst according to the liquid phase method. More specifically, an autoclave having a capacity of 200 ml was charged with 90 g (5.0 moles) of water, 2 g of the above catalyst and 9.0 g (0.321 mole) of ethylene. The mixture was heated at 250° C. with stirring for 2 hours to effect reaction. The pressure was about 130 kg/cm$^2$.

After completion of the reaction, the reaction mixture was cooled to room temperature and then the catalyst was separated by filtration. The reaction liquid was analyzed by gas chromatography. It was found that 2.15 g (0.0467 mole) of ethanol was produced. The conversion of ethylene to ethanol was 14.5%. Minute amounts of acetaldehyde and acetone were produced in addition to ethanol but production of other products was not observed. The selectivity based on ethylene was 99.0% to ethanol, 0.7% to acetaldehyde and 0.3% to acetone.

EXAMPLE 15

Hydration of propylene was carried out by using the same catalyst as used in Example 14. More specifically, an autoclave having a capacity of 200 ml was charged with 2 g of the catalyst, 90 g (5.0 moles) of water and 9.0 g (0.214 mole) of propylene. The mixture was heated at 180° C. with stirring for 2 hours to effect reaction. The pressure was about 70 kg/cm$^2$.

After completion of the reaction, the reaction mixture was cooled to room temperature, and then the catalyst was separated by filtration. The reaction liquid was analyzed by gas chromatography. It was confirmed that 1.17 g (0.0195 mole) of isopropanol was produced. The conversion of propylene to ispropanol was 9.1%. A minute amount of acetone as produced in addition to isopropanol. The selectivity to isopropanol was 99.5%.

EXAMPLE 16

Erionite was synthesized according to a process disclosed in Japanese Examined Patent Publication No. 50-23,400. More specifically, 17.3 g of benzyltrimethylammonium chloride (having a purity of 95% by weight), 36.8 g of sodium hydroxide (having a purity of 98% by weight), 8.4 g of potassium hydroxide (having a purity of 85% by weight) and 17.2 g of sodium aluminate (comprising 32.98% by weight of $AL_2O_3$ and 35.13% by weight of $Na_2O$) were dissolved in 226.6 g of water. Then, 318.2 g of silica sol (comprising 30% by weight of $SiO_2$ and 0.45% by weight of $Na_2O$) was added to the solution to form a reaction mixture having the following molar ratios:

$R^+/(R^+ + Na^+ + K^+) = 0.065$, $(Na^+ + K^+)/SiO_2 = 0.80$, $H_2O/(Na^+ + K^+) = 20.3$, $SiO_2/Al_2O_3 = 28.6$, and $K^+/(Na^+ + K^+) = 0.10$, wherein R stands for benzyltrimethylammonium cation.

This reaction mixture as charged in an autoclave having a capacity of 1 liter and was heated at 100° C. for 13 days according to the standing method to effect crystallization. The reaction mixture was cooled to room temperature, and the formed solid crystal was recovered by filtration, washed and then dried.

From the results of the X-ray diffractometry using a copper Kα ray, it was found that the crystal powder had an X-ray diffraction pattern shown in Table 10.

TABLE 10

Results of X-Ray Diffractometry of Zeolite of Example 16

| Diffraction Angle 2θ ±0.2° | Lattice Spacing d ±0.2 (Å) | Refractive Intensity I/Io |
|---|---|---|
| 7.7 | 11.4 | 100 |
| 9.6 | 9.2 | 6 |
| 11.7 | 7.6 | 13 |
| 13.4 | 6.6 | 55 |
| 14.0 | 6.3 | 11 |
| 15.5 | 5.7 | 17 |
| 16.5 | 5.4 | 9 |
| 17.8 | 5.0 | 3 |
| 19.4 | 4.6 | 15 |
| 20.5 | 4.3 | 72 |
| 21.3 | 4.2 | 15 |
| 23.3 | 3.8 | 50 |
| 23.7 | 3.7 | 74 |
| 24.8 | 3.6 | 34 |
| 26.1 | 3.4 | 4 |
| 27.0 | 3.3 | 22 |
| 28.2 | 3.2 | 27 |
| 28.7 | 3.1 | 3 |
| 30.5 | 2.9 | 10 |
| 31.4 | 2.8 | 62 |
| 31.8 | 2.8 | 20 |
| 33.5 | 2.7 | 19 |
| 36.0 | 2.5 | 15 |
| 36.2 | 2.5 | 15 |
| 38.2 | 2.4 | 3 |
| 39.4 | 2.3 | 3 |

The zeolite was calcined at 540° C. for 5 hours in air. The adsorption properties of the zeolite were measured at 25° C. and 48 mmHg. It was found that the n-hexane adsorption capacity was 7.1% by weight and the cyclohexane adsorption capacity was 1.6% by weight. Namely, this zeolite is characterized in that the cyclohexane adsorption capacity is considerably smaller than the n-hexane adsorption capacity.

The crystal powder was subjected to the ion exchange in an aqueous 2N ammonium chloride solution at 90° C. for 5 hours. The crystal was washed with water, dried and calcined again in air at 540° C. for 5 hours. From the results of the elementary analysis, it was found that the product had a composition represented by the following molar ratio formula:

$0.003Na_2O \cdot 0.24K_2O \cdot Al_2O_3 \cdot 7.2SiO_2 \cdot 5.4H_2O$.

From the results of the powder X-ray diffractometry, it was confirmed that the X-ray diffraction pattern as observed after the ion exchange treatment was substantially the same as that as observed before the ion exchange treatment.

Hydration of ethylene was carried out by using the so-obtained zeolite crystal powder as the catalyst. More specifically, an autoclave having a capacity of 200 ml was charged with 90 g (5.0 moles) of water, 2 g of the above catalyst and 8.6 g (0.307 mole) of ethylene. The mixture was heated at 240° C. with stirring for 3 hours to effect reaction. The pressure was about 120 kg/cm$^2$.

After completion of the reaction, the reaction mixture was cooled to room temperature and then the catalyst was separated by filtration. The reaction liquid was analyzed by gas chromatography. It was found that 2.56 g (0.0557 mole) of ethanol was produced. The conversion of ethylene to ethanol was 18.1%. Minute amounts of acetaldehyde and acetone were produced in addition to ethanol but production of other products was not observed. The selectivity based on ethylene was 98.9% to ethanol, 0.9% to acetaldehyde and 0.2% to acetone.

EXAMPLE 17

Hydration of propylene was carried out by using the same catalyst as used in Example 16. More specifically, an autoclave having a capacity of 200 ml was charged with 2 g of catalyst, 90 g (5.0 moles) of water and 9.2 g (0.219 mole) of propylene. The mixture was heated at 180° C. with stirring for 3 hours to effect reaction. The pressure was about 70 kg/cm$^2$.

After completion of the reaction, the reaction mixture was cooled to room temperature, and then the catalyst was separated by filtration. The reaction liquid was analyzed by gas chromatography. It was confirmed that 1.70 g (0.0283 mole) of isopropanol was produced. The conversion of propylene to isopropanol was 12.9%. A minute amount of acetone was produced in addition to isopropanol. The selectivity to isopropanol was 99.3%.

EXAMPLE 18

Hydration of isobutene was carried out by using the same catalyst as used in Example 16. More specifically, an autoclave having a capacity of 200 ml was charged with 2 g of the catalyst, 90 g (5.0 moles) of water and 14.7 g (0.263 mole) of isobutene. The mixture was heated at 120° C. with stirring for 3 hours to effect reaction. The pressure was about 20 kg/cm$^2$.

After completion of the reaction, the reaction mixture was cooled to room temperature, and then the catalyst was separated by filtration. The reaction liquid was analyzed by gas chromatography. It was confirmed that 1.46 g (0.0197 mole) of t-butanol was produced. The conversion of isobutene to t-butanol was 7.5%. The selectivity to t-butanol was 100%.

EXAMPLE 19

The hydrogen type crystal powder obtained in Example 14 was mixed with silica sol in an amount of 20% by weight as SiO$_2$, and 5% by weight of graphite was further added. The mixture was molded to a tablet having a diameter of 5 mm and a height of 5 mm. The molded product was calcined in air at 540° C. for 3 hours to form a catalyst.

Hydration of ethylene was carried out under pressure by using a fixed bed reaction apparatus according to the phase method. More specifically, using 20 ml of the catalyst packed in a reaction tube, reaction was carried out at a temprature of 250° C., a pressure of 70 kg/cm$^2$, a water/ethylene molar ratio of 0.6 and a liquid hourly space velocity of water and ethylene of 1.0 hr$^{-1}$. The reaction product was sampled at predetermined intervals and analyzed by gas chromatography. It was found that the conversion of ethylene to ethanol was 6.0%, and the reaction was not particularly changed with time on stream. Minute amounts of acetaldehyde and acetone were produced in addition to ethanol but other products were not produced. The selectivity to ethanol was 98.7%.

EXAMPLE 20

Hydration of propylene was carried out by using the same catalyst as used in Example 19 in the same manner as described in Example 19. More specifically, using 20 ml of the catalyst packed in a reaction tube reaction was carried out at a temperature of 180° C., a pressure of about 20 kg/cm$^2$, a water/propylene molar ratio of 1 and a liquid hourly space velocity of water and propylene of 1.0 hr$^{-1}$. The conversion of propylene to isopropanol was 5.8%. A minute amount of acetone was formed in addition to isopropanol. The selectivity to isopropanol was 99.6%.

EXAMPLE 21

Hydration of butene-1 was carried out by using the same catalyst as used in Example 20 in the same manner as described in example 20. More specifically, using 20 ml of the catalyst packed in a reaction tube, reaction was carried out at a temperature of 160° C., a pressure of about 10 kg/cm$^2$, a water/butene-1 molar ratio of 1 and a liquid hourly space velocity of water and butene-1 of 1.0 hr$^{-1}$. The conversion of butene-1 to sec-butanol was 2.7%. The selectivity to sec-butanol was 99.8%.

We claim:

1. A process for the preparation of alcohols by catalytically hydrating olefins wherein at least one crystalline aluminosilicate selected from the group consisting of offretite, ferrierite and erionite is used as a catalyst.

2. A process according to claim 1, wherein at least a part of the exchangeable cations in each of the offretite and ferrierite is exchanged with at least one cation selected from the group consisting of a hydrogen ion, an alkaline earth metal ion and a rare earth metal ion.

3. A process according to claim 1, wherein at least 30% of the exchangeable cations is exchanged.

4. A process according to claim 1, wherein at least a part of the exchangeable cations in the erionite is ion-exchanged with at least one cation selected from the group consisting of a hydrogen ion, an ammonium ion, an alkali metal ion, an alkaline earth metal ion and a rare earth metal ion.

5. A process according to claim 1, wherein at least 30% of the exchangeable cations is exchanged.

6. A process according to claim 1, wherein the crystalline aluminosilicate is offretite characterized by an X-ray diffraction pattern shown in Table 1.

7. A process according to claim 1, wherein the crystalline aluminosilicate is ferrierite characterized by an X-ray diffraction pattern shown in Table 2.

8. A process according to claim 1, wherein the crystalline aluminosilicate is erionite characterized by an X-ray diffraction pattern substantially shown in Table 3.

9. A process according to claim 1, wherein the erionite is synthetic erionite.

10. A process according to claim 4, wherein the erionite is one synthesized according to a process in the absence of an organic mineralizer.

11. A process according to claim 1, wherein the crystalline aluminosilicate contains at least one element selected from chromium, manganese, iron, copper, zinc, phosphorus, molybdenum, tungsten, tin, antimony and bismuth.

12. A process according to claim 1, wherein the olefin is one having 2 to 8 carbon atoms.

13. A process according to claim 12, wherein the olefin is ethylene, propylene or butene.

14. A process according to claim 1, wherein the olefin is hydrated at a temperature of about 50° C. to about 350° C. under a pressure of about 1 to about 300 atmospheres at a water/olefin molar ratio of from 0.2 to 100.

15. A process according to claim 1, wherein the olefin is hydrated at a temperature of about 100° to about 300° C. under a pressure of about 1 to about 250 atmospheres at a water/olefin molar ratio of from about 0.3 to about 50.

16. A process according to claim 1, wherein the crystalline aluminosilicate is offretite characterized by an X-ray diffraction pattern shown in Table 7.

17. A process according to claim 1, wherein the crystalline aluminosilicate is ferrierite characterized by an X-ray diffraction pattern shown in Table 8.

18. A process according to claim 1, wherein the crystalline aluminosilicate is ferrierite characterized by an X-ray diffraction pattern shown in Table 9.

* * * * *